US00PP10350P

United States Patent [19]

Utecht

[11] Patent Number: Plant 10,350

[45] Date of Patent: Apr. 21, 1998

[54] GERANIUM PLANT NAMED 'FISPUR'

[75] Inventor: Angelika Utecht, Montabaur, Germany

[73] Assignee: Florfis AG, Binningen, Switzerland

[21] Appl. No.: 754,364

[22] Filed: Nov. 22, 1996

[51] Int. Cl.[6] ..... A01H 5/00

[52] U.S. Cl. ..... Plt./87.12

[58] Field of Search ..... Plt./87.12

[56] References Cited

PUBLICATIONS

GTITNLUPOVROM Citation DE PBR PEL01008 for 'Fispur', Dec. 18, 1995.

GTITMUPOVROM Citation CA PBR 96–794 for 'Fispur', Jul. 29, 1996.

*Primary Examiner*—James R. Feyrer

*Attorney, Agent, or Firm*—Foley & Lardner

[57] ABSTRACT

A new and distinct cultivar of geranium plant named 'Fispur', particularly characterized by the combined features of cherry red flower color, weakly semi-double, nearly round flower form, medium green foliage with distinct zonation, medium vigorous, but comparatively compact plant habit, and early to medium spring flower response.

1 Drawing Sheet

The present invention comprises a new and distinct cultivar of geranium, botanically known as *Pelargonium zonale*, and hereinafter referred to by the cultivar name 'Fispur'.

'Fispur' is a product of a planned breeding program which had the objective of creating new geranium cultivars with red flower color, medium green, zoned foliage, and medium tall plant habit.

'Fispur' was originated from a hybridization made by the inventor Angelika Utecht in a controlled breeding program in Galdar, Gran Canaria, Spain, in 1991. The female parent was the cultivar 'Fisnida' characterized by its single orange-red flowers, medium green foliage with distinct zonation, and medium to vigorous growth. The male parent of 'Fispur' was the commercial variety 'Penve', having pink-violet semi-double flowers, slightly zoned foliage, and compact growth habit.

'Fispur' was discovered and selected as one flowering plant within the progeny of the stated cross by Angelika Utecht in 1992 in a controlled environment in Galdar, Gran Canaria, Spain. The first act of asexual reproduction of 'Fispur' was accomplished when vegetative cuttings were taken from the initial selection in Autumn 1992 in a controlled environment in Galdar, Gran Canaria, Spain, by, or under the supervision of, Angelika Utecht.

Horticultural examination of plants grown from these cuttings, initiated in May 1993 in Hillscheid, Federal Republic of Germany and continuing thereafter, has demonstrated that the combination of characteristics as herein disclosed for 'Fispur' are firmly fixed and are retained through successive generations of asexual reproduction.

'Fispur' has not been observed under all possible environmental conditions. The phenotype may vary significantly with variations in environment such as temperature, light intensity and day length, without, however, any variation in genotype.

The following observations, measurements, and comparisons describe plants grown in Hillscheid, Federal Republic of Germany under greenhouse conditions which approximate those generally used in commercial practice.

The following traits have been repeatedly observed and are determined to be basic characteristics of 'Fispur', which in combination distinguish this geranium as a new and distinct cultivar:

1. Light cherry red flower color.
2. Round, open semi-double flowers.

3. Medium green foliage with distinct zonation.
4. Medium growth characteristics and compact plant habit.
5. Early to medium spring flower response.

Of the many commercial cultivars known to the present inventor, the most similar in comparison to 'Fispur' are the commercial varieties 'Fismag', disclosed in U.S. Plant Pat. No. 8,725, 'Disco', disclosed in U.S. Plant Pat. No. 5,930, and 'Fisbraris', disclosed in pending application Ser. No. 08/548,893.

In general comparison to 'Fismag', 'Fispur' has a slightly lighter flower color, the shape of its florets is more round and closed, and its foliage is somewhat more distinctly zoned. In addition, plants of 'Fispur' have a shorter habit during the summer. In contrast, 'Fismag' grows taller during the summer, and its umbels are higher above the foliage.

In contrast to 'Disco', 'Fispur' has distinctly zoned foliage. In addition, the flowers of 'Fispur' lack the purple eyes on its petals and its umbels are comparatively wide and flat. By contrast, the umbels of 'Disco' are almost spherically shaped and borne higher above the foliage.

In comparison to 'Fisbraris', flowers of 'Fispur' lack the distinct red eyes of 'Fisbraris', and its foliage is medium green, in contrast to the dark green leaves of 'Fisbraris'. The plant habit of 'Fispur' with inflorescences is taller than 'Fisbraris'.

The accompanying photographic drawing shows typical flower and foliage characteristics of 'Fispur', with colors being as true as possible with illustrations of this type.

In the following description color references are made to The Royal Horticultural Society Colour Chart (R.H.S.). The color values were determined indoors from flowers taken from plants grown in a greenhouse in May 1995 in Hillscheid, Germany.

Classification:

*Botanical.*—A hybrid of the species *Pelargonium zonale l'hert.*

*Commercial.*—Zonal geranium, cv. 'Fispur'.

Inflorescence:

*Umbel.*—Shape: Flat semi-spherical. Average diameter: 109 mm. Average depth: 60 mm. Peduncle length: 152 mm. Color of peduncle: Green, slightly anthocyanin colored. Pedicel length: 27 mm. Pedical color: Light to dark red. Number of flowrs per umbel: About 35–45.

*Corolla.*—Average diameter: 46 mm. Form: Semi-double. Number of petals: 7–8. Number of petaloids: 1–2. Color (General tonality from a distance of three meters): Light cherry red. Color of upper petals: Between 57 B and 52 A. Markings on upper petals: No distinct markings. Color of lower petals: 57 C. Color of lower surface of petals: 52 A. Color of sepals: Green. Number of sepals: 5.

*Bud.*—Shape: Round to elliptic. Color (adaxial): Green Color (abaxial): Rose-red

*Reproductive organs.*—Androecium: 7 fertile anthers, white filaments, orange pollen. Gynoecium: 5–6 lobed stigma, light red style and stigma. Seed set: A few seeds occasionally are produced.

*Spring flowering response period.*—In Hillscheid, Germany in 1995 plants had on average 1.1 flowers opened 11 weeks after planting of unrooted cuttings.

*Outdoor flower production.*—The flower count in 1994 in Hillscheid, Germany indicated about 28 umbels per plant for May through August observation period.

*Durability.*—Good shatter resistance.

Plant:

*Foliage.*—Form: Kidney-shaped. Margin: Bicrenated. Size of leaf: 94 mm. Color of upper surface: Medium green, approximately 137 C-D. Color of zonation: Brown, about 166 A. Tolerance of botrytis: Average.

*General appearance and form.*—Internode length: 20–30 mm. Branching pattern: 6.6 branches per plant, on 12 week old plants. Height of foliage: 17 cm in June, based on 16 week old plants.

I claim:

1. A new and distinct cultivar of geranium plant named 'Fispur', as illustrated and described.

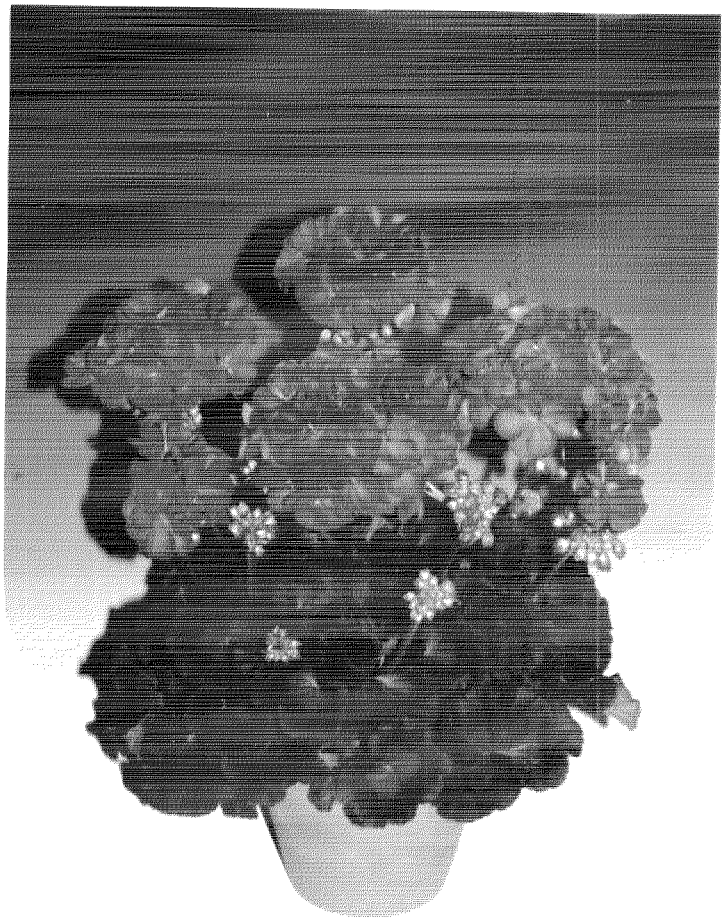

* * * * *